United States Patent [19]

Safi

[11] Patent Number: 4,931,401
[45] Date of Patent: Jun. 5, 1990

[54] BIOREACTOR

[75] Inventor: Bechara F. Safi, Cartierville, Canada

[73] Assignee: La Societe De Recherche Snc Inc., Canada

[21] Appl. No.: 239,541

[22] Filed: Sep. 1, 1988

[51] Int. Cl.$^5$ ............................................ C12M 1/00
[52] U.S. Cl. .................................. 435/287; 435/819;
422/142; 422/143; 422/311; 261/113;
261/114.2; 210/150; 210/616; 210/618
[58] Field of Search ............... 435/285, 287, 309, 310,
435/819; 422/142, 143, 311; 261/113, 114.2;
210/150, 151, 603, 606, 610, 617, 618

[56] References Cited

U.S. PATENT DOCUMENTS

| | | | |
|---|---|---|---|
| 1,738,386 | 12/1929 | Morrell | 261/114.2 X |
| 2,378,952 | 6/1945 | Rousseau | 261/114.2 |
| 3,475,134 | 10/1969 | Weber et al. | 261/114.2 X |
| 3,743,582 | 7/1973 | Kitai et al. | 435/310 X |
| 3,746,516 | 7/1973 | Michaud | 422/143 X |
| 4,589,841 | 5/1986 | Bergkrist | 431/170 |
| 4,604,050 | 8/1986 | Henriksson | 431/170 X |
| 4,654,308 | 3/1987 | Safi et al. | 435/310 |
| 4,670,140 | 6/1987 | Aivasidis et al. | 435/819 X |

FOREIGN PATENT DOCUMENTS

| | | | |
|---|---|---|---|
| 2151574 | 5/1973 | Fed. Rep. of Germany | 435/313 |
| 2017752 | 10/1979 | United Kingdom | 435/310 |

*Primary Examiner*—Carl D. Price
*Attorney, Agent, or Firm*—Steele, Gould & Fried

[57] ABSTRACT

The disclosure herein describes a bioreactor for the biochemical treatment of liquids containing organic matter. It comprises a container with an inlet for receiving liquid to be treated with at least one horizontal plate to support a bed of microorganism cells which react with the organic matter to form a volatile gas. An aperture is provided in the plate to provide liquid flow communication between upper and lower compartments on either sides of the plate. A blockage element extends over the aperture to prevent the liquid and the microorganism cells from returning through the aperture to the lower compartment. An outlet is provided for releasing the gas from the container while a further outlet is used for releasing treated liquid.

6 Claims, 2 Drawing Sheets

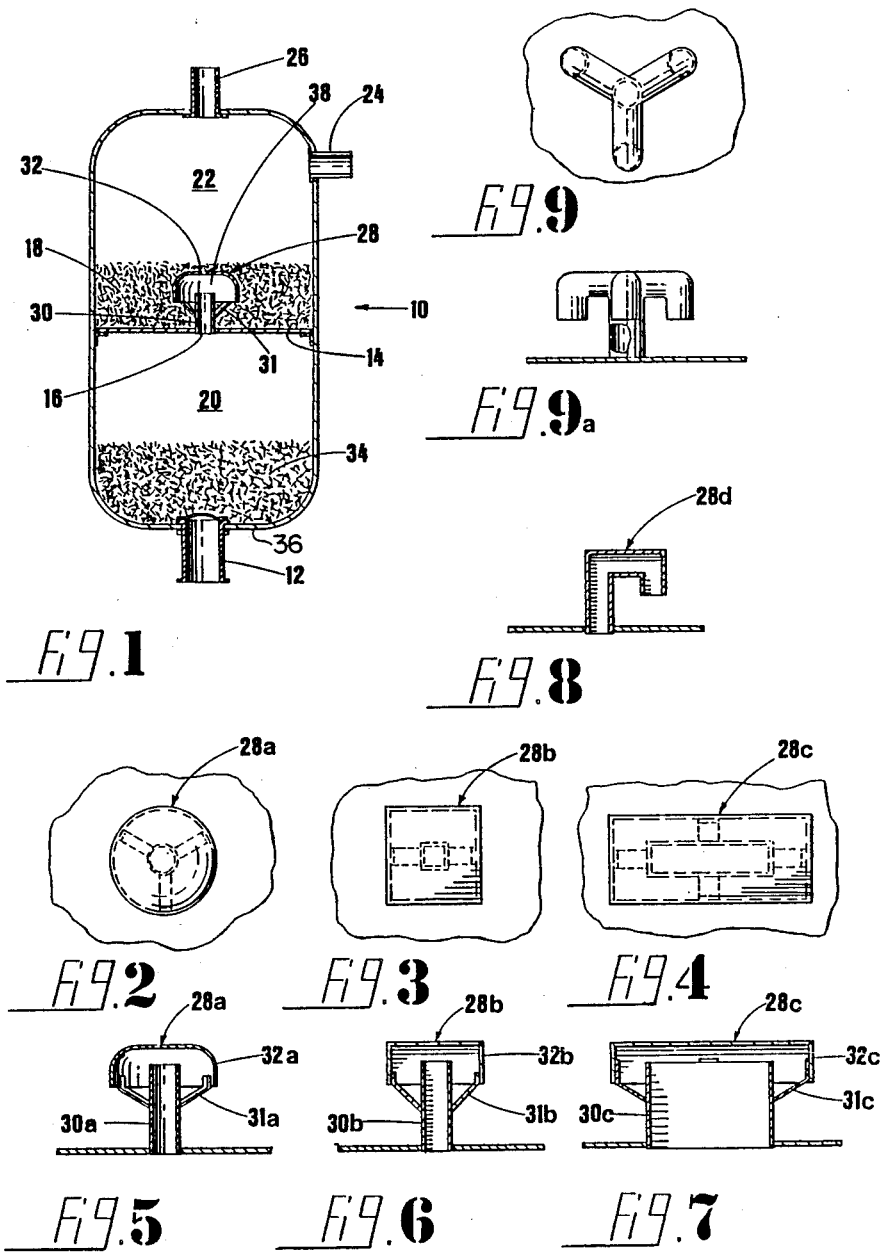

4,931,401

BIOREACTOR

FIELD OF THE INVENTION

The present invention relates to a bioreactor for the biochemical treatment of liquids containing organic matter.

BACKGROUND OF THE INVENTION

A bioreactor for such treatment of liquids is described in U.S. Pat. 4,654,308 issued Mar. 31, 1987 to Safi et al. This patent describes the need to treat liquids containing organic matter, such as in the pulp and paper industry or the cheese processing industry due to pollution regulations imposed by governments.

When a substrate, during anaerobic treatment, comes into contact with microorganisms, it is converted into gas by means of two principal reactions which occur in sequence.

The first reaction to occur, known as acidogenesis reaction, is when the substrate is converted to volatile acids due to the action of the acidogenesis microorganisms. In this reaction, the rate of conversion into acids of the substrate is proportional to the concentration of the substrate.

The second reaction, known as methanogenesis reaction, occurs when the volatile acids, through the action of methanogenesis micro-organisms, are converted into methane (biogas). In this reaction, the rate of conversion of the volatile acids into methane is inversely proportionate to the concentration of volatile acids.

In general, both described reactions occur sequentially in the same reactor.

The bioreactor defined in the above mentioned U.S. patent consists of a tubular container with a plurality of spaced apart trays, each tray being apertured to provide liquid flow communication between the inlet and outlet with apertures of alternate trays being arranged relative to one another to cause the liquid to flow laterally across the respective cell beds of the trays as the liquid flows from one tray to another. It has been found, however, that there is a possibility for the fluid and the microorganism cells to return to the lower compartment, thus greatly reducing the efficiency of the reactor.

OBJECTS AND STATEMENT OF THE INVENTION

It is an object of the present invention to provide a flow reactor which overcomes the above described problem associated with presently known bioreactors.

The present invention relates to a bioreactor for the biochemical treatment of liquids containing organic matter which comprises:

an upstanding container having inlet means for receiving liquids to be treated and outlet means for discharging liquids once treated;

plate means in the container defining, on either side of the plate means, upper and lower compartments;

a bed of microorganism cells supported on the plate means in the upper compartment, the cells being capable of reacting with the organic matter to form a volatile gas; the plate means having aperture means therethrough to provide liquid flow communication between the upper and lower compartments;

blockage means in the upper compartment, associated with the aperture, for preventing the liquid and microorganism cells from returning through the aperture means to the lower compartment; and means for releasing the gas from the container.

According to a preferred embodiment of the invention, the blockage means comprise a tubular portion extending upwardly from the aperture means and a cap portion extending above the open end of the tubular portion. The area between the cap portion and the tubular portion is filled with part of the gas formed by the reaction of the cells with the organic matter, this gas-filled area acting as a stopper to prevent the return of the liquid, cells and gas in the adjacent lower compartment.

According to another preferred embodiment, baffle means are mounted under the plate means in the area of the aperture means to improve the hydrology of the reactor.

Other objects and further scope of applicability of the present invention will become more readily apparent from the following description of preferred embodiments. It should be understood, however, that this detailed description, while indicating preferred embodiments is given by way of illustration only, since various changes and modifications within the spirit and scope of the invention will become apparent to those skilled in the art.

BRIEF DESCRIPTION OF THE DRAWINGS

FIG. 1 is a schematic longitudinal sectional view of a bioreactor according to the present invention;

FIGS. 2, 3 and 4 are top plan views of three embodiments of blockage means used with the present invention;

FIGS. 5, 6 and 7 are elevational views of the blockage means illustrated in FIGS. 2, 3 and 4 respectively;

FIG. 8 is a cross-sectional view of another embodiement of the blockage means;

FIGS. 9 and 9a are top and elevational views of another embodiment of the blockage means;

DESCRIPTION OF PREFERRED EMBODIMENTS

Figure 10:
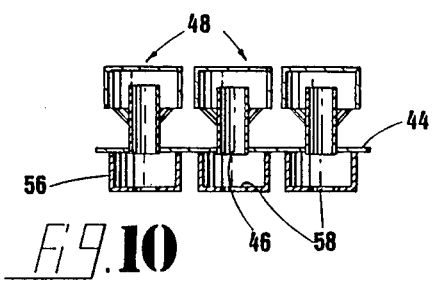
FIG. 10 is a cross-sectional elevation of blockage and baffle means used with the present invention.

Referring to FIG. 1, there is shown schematically a bioreactor 10 for the biochemical treatment of liquids containing organic matter. An inlet line 12 allows the liquids to be received at the bottom of the container. The container comprises an intermediate horizontal plate 14 having a central aperture 16. A bed 18 of microorganism cells is supported on the plate.

The plate 14 divides the container 10 into two compartments 20 and 22. In the upper compartment 22, a first outlet 24 is provided for discharging treated liquid while a second outlet 26 is used for discharging the volatile gas which is formed by the reaction of the liquid with the microorganism cells.

According to the present invention, a blockage element, generally denoted 28, is provided over aperture 16 of the plate and comprises a tubular portion 30 extending upwardly from the aperture 16 and a cap portion 32 extending over the tubular portion 30 and supported thereto by means of three arms 31.

Preferably, the container 10 comprises also a bed of microorganism cells 34 resting on the bottom wall 36 of the container 10.

The reactor shown in FIG. 1 functions in the following manner. The liquid to be treated enters the container 10 via inlet 12 and reacts with the microorganism cells of the bed 34 of the lower compartment 20. Continuous flow of liquid in the container causes the treated liquid and the gas formed by the reaction to pass to the upper compartment 22 through aperture 16 where the liquid again reacts with the second bed 18 of microorganism cells. The liquid thus treated exits at outlet 24 while the volatile gas exits at outlet 26.

The blockage element 28 acts as a "check valve" to prevent the liquid and the microorganism cells in the upper compartment to return to the lower compartment 20 through the aperture. The area situated under the cap portion 32 is filled with gas resulting from the reaction of the first cell bed 34 with the liquids.

FIGS. 2, 3 and 4 show various shapes of blockage elements 28a, 28b, 28c which may be used with the present invention. In FIG. 2, the blockage element takes the shape of an inverted cup member 32a while the blockage element of FIGS. 3 and 4, 32b and 32c are respectively square and rectangular shaped inverted bodies.

The blockage element 28d of FIG. 8 takes the form of an inverted U-shaped tubular member 40 while, in FIG. 9, the blockage element has a T-shape with opposite branches 42a and 42b.

Figure 11:
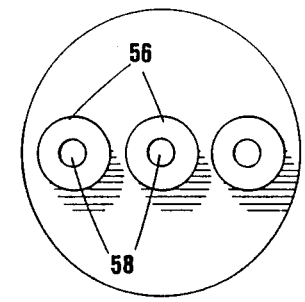
FIG. 11 is a bottom plan view of that illustrated in FIG. 10.

Referring to FIGS. 10 and 11, the hydrology between adjacent compartments may be improved by disposing, under the plate, a plurality of baffle means. In the embodiment illustrated in these figures, plate 44 displays a series of apertures 46, each receiving thereover a blockage element 48 situated in the upper compartment of a container. In the lower compartment, underneath plate 44, a plurality of baffle members 56 in the shape of cylindrical bodies have a lower opening 58 in registry with aperture 46. These baffle members may have various shapes.

Figure 12:
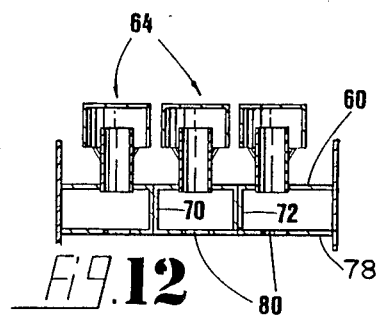
FIG. 12 is a cross-sectional elevation illustrating another embodiment of baffle means used with the present invention.
Figure 13:
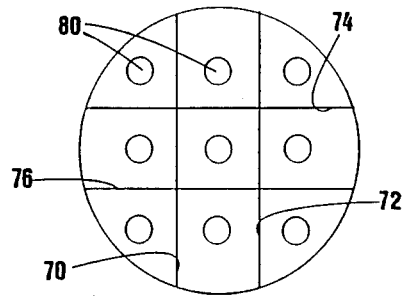
FIG. 13 is a bottom plan view of the embodiment illustrated in FIG. 12.

FIGS. 12 and 13 show another embodiment of baffle members used with the present invention. The plate 60 of the reactor includes a plurality of blockage elements 64 extending in the upper compartment while, in the lower compartment, a baffle member extends under the full area of the plate and includes a matrix of dividing walls 70, 72, 74, 76 and a bottom wall 78 with an opening 80 in each compartment formed by the matrix.

Figure 14:
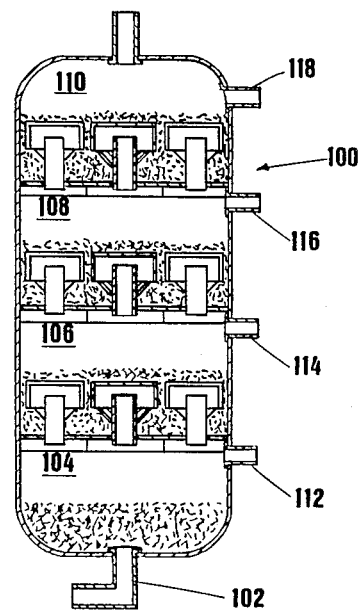
FIG. 14 shows an elevational view of another embodiment of a reactor made in accordance with the present invention.

FIG. 14 shows another variation of a bioreactor made in accordance with the present invention. Body 100 of the container has an inlet 102 for the liquid to be treated and a series of vertically spaced compartments 104, 106, 108 and 110, each including a bed of microorganism cells and blockage means as described above. However, in the present embodiment, a series of outlets 112, 114, 116 and 118 are provided for the outlet of the volatile gas from each compartment.

Although the invention has been described above with respect to various forms of the invention, it will be evident that it may be modified and varied in various ways. For example, there may be provided a liquid inlet for each compartment rather than a single inlet at the bottom as illustrated. Further, these inlets may enter each compartment in the bed of microorganism cells or thereabove. It is therefore wished to have it understood that the present invention should not be limited in interpretation except by the terms of the following claims.

The embodiments of the invention in which an exclusive property or privilege is claimed are defined as follows:

1. A bioreactor for the biochemical treatment of liquids containing organic matter, comprising:
    an upstanding container having inlet means for receiving liquid to be treated;
    a plurality of vertically spaced plate means extending horizontally in said container defining a plurality of compartments, each said plate means having aperture means therethrough to provide liquid flow communication between adjacent compartments, wherein said aperture means include a series of apertures evenly distributed over the area of said plate means;
    a bed of microorganism cells supported on each said plate means and capable of reacting with said organic matter to form a volatile gas;
    blockage means in each said compartment extending above said aperture means for preventing said liquid and microorganism cells from passing through said aperture means and returning to a lower adjacent compartment;
    an outlet port in each compartment above said bed of microorganism cells;
    baffle means mounted under said plate means at said aperture means for limiting the flow of volatile gas to an upper compartment, wherein said baffle means defines a baffle member extending the entire dimension of said plate means;
    said member defining a series of openings therein allowing gas to pass through said member and subsequently into a corresponding one of said apertures of said plate means;
    the volatile gas deflected by the baffle means exiting through said outlet port of said compartment; and
    outlet means for discharging treated liquid from said container.

2. A bioreactor as defined in claim 1, wherein said inlet means consist of a liquid feed port in the lowermost compartment of the container.

3. A bioreactor as defined in claim 1, said inlet means further including a liquid feed port in one or more of the remaining compartments of the container.

4. A bioreactor as defined in claim 1, wherein said container has a bottom wall and a bed of microorganism cells supported on said bottom wall, said inlet means consisting of a liquid feed part in said bottom wall.

5. A bioreactor as defined in claim 1, wherein said blockage means comprise a tubular portion extending upwardly from said aperture means and having an upper open end, and a cap portion extending above said open end; an area below said cap portion being filled with gas formed by the reaction of the cells with said organic matter, said gas filled area acting as a stopper to prevent the return of the liquid and cells in an adjacent lower compartment.

6. A bioreactor as defined in claim 1, wherein said container is a tubular tank.

* * * * *

UNITED STATES PATENT AND TRADEMARK OFFICE
CERTIFICATE OF CORRECTION

PATENT NO. : 4,931,401

DATED : June 5, 1990

INVENTOR(S) : Bechara F. Safi

It is certified that error appears in the above-identified patent and that said Letters Patent is hereby corrected as shown below:

In Claim 4, column 4, line 55, that portion of the line stating "part" should state --port--.

Signed and Sealed this

Fifth Day of November, 1991

Attest:

HARRY F. MANBECK, JR.

Attesting Officer

Commissioner of Patents and Trademarks